United States Patent
Asif et al.

(10) Patent No.: US 10,552,664 B2
(45) Date of Patent: Feb. 4, 2020

(54) IMAGE FEATURE CLASSIFICATION AND LOCALIZATION USING DISCRIMINATIVE REPRESENTATIONS FOR ROBOTIC SURGICAL CONTROL

(71) Applicant: INTERNATIONAL BUSINESS MACHINES CORPORATION, Armonk, NY (US)

(72) Inventors: Umar Asif, Melbourne (AU); Stefan Harrer, Melbourne (AU); Jianbin Tang, Melbourne (AU); Antonio Jimeno Yepes, Melbourne (AU)

(73) Assignee: INTERNATIONAL BUSINESS MACHINES CORPORATION, Armonk, NY (US)

( * ) Notice: Subject to any disclaimer, the term of this patent is extended or adjusted under 35 U.S.C. 154(b) by 112 days.

(21) Appl. No.: 15/821,950

(22) Filed: Nov. 24, 2017

(65) Prior Publication Data

US 2019/0163955 A1    May 30, 2019

(51) Int. Cl.
*G06K 9/00*      (2006.01)
*G06K 9/62*      (2006.01)
(Continued)

(52) U.S. Cl.
CPC .......... *G06K 9/00147* (2013.01); *A61B 6/502* (2013.01); *A61B 6/5217* (2013.01);
(Continued)

(58) Field of Classification Search
None
See application file for complete search history.

(56) References Cited

U.S. PATENT DOCUMENTS 7,421,415 B2    9/2008  Dong et al.
8,638,998 B2    1/2014  Steines et al.
(Continued)

FOREIGN PATENT DOCUMENTS

| CN | 103325140 | 9/2013 |
| CN | 105387818 | 3/2016 |
| EP | 0 041 749 | 12/1981 |

OTHER PUBLICATIONS

Zhou et al., "Image Classification Using Biomimetic Pattern Recognition with Convolutional Neural Networks Features", Computational Intelligence and Neuroscience, vol. 2017, Article ID 3792805, pp. 1-12.

*Primary Examiner* — Tahmina N Ansari
(74) *Attorney, Agent, or Firm* — F. Chau & Associates, LLC

(57) ABSTRACT

A method for digital image classification and localization includes receiving a digital image of a biological organism from an imaging apparatus, the digital image comprising a plurality of intensities on a 2-dimensional grid of points, generating a plurality of discriminative representations of the 2D digital image by extracting dominant characteristics of the image from three different viewpoints, where the plurality of discriminative representations form a 3-dimensional digital image, combining the 3D digital image with the 2D digital image in a convolutional neural network that outputs a 3-channel feature map that localizes image abnormalities in each of the three channels and includes a detection confidence that each abnormalities is a neoplasm, providing the 3-channel feature map to a controller of a robotic surgical device where the robotic surgical device uses the 3-channel feature map to locate the neoplasm within the biological organism in a surgical procedure for treating the neoplasm.

10 Claims, 5 Drawing Sheets

(51) Int. Cl.
*A61B 6/00* (2006.01)
*G06T 7/00* (2017.01)
*A61B 34/32* (2016.01)
*A61B 34/10* (2016.01)

(52) U.S. Cl.
CPC .............. *A61B 34/10* (2016.02); *A61B 34/32* (2016.02); *G06K 9/0014* (2013.01); *G06K 9/6228* (2013.01); *G06K 9/6289* (2013.01); *G06T 7/0014* (2013.01); *A61B 2034/107* (2016.02); *G06T 2207/20084* (2013.01); *G06T 2207/30068* (2013.01); *G06T 2207/30096* (2013.01)

(56) References Cited

U.S. PATENT DOCUMENTS

| | | |
|---|---|---|
| 8,908,950 B2 | 12/2014 | Barfuss et al. |
| 2012/0189176 A1 | 7/2012 | Giger et al. |
| 2017/0103299 A1 | 4/2017 | Aydonat et al. |
| 2018/0129893 A1* | 5/2018 | Son .................... G06K 9/00979 |
| 2018/0165809 A1* | 6/2018 | Stanitsas ............... G06F 3/0484 |

* cited by examiner

IMAGE FEATURE CLASSIFICATION AND LOCALIZATION USING DISCRIMINATIVE REPRESENTATIONS FOR ROBOTIC SURGICAL CONTROL

TECHNICAL FIELD

Embodiments of the present disclosure are directed to methods for systems and methods for image classification and localization.

DISCUSSION OF THE RELATED ART

The availability of enormous training data is one of the key factors for the success of deep learning methods for several classification tasks. However, in many real world image classification problems, the available labelled data is either insufficient or too imbalanced to be able to train accurate and robust classification models. For example, in the task of cancer classification/localization, most of the images do not show cancer.

To alleviate this situation, a common approach is data augmentation, which involves the transformation of the training data to generate new samples that can improve the accuracy and robustness of classification models. Examples of data transformation include augmenting data through affine/geometric transformations, adding noise or through extracting image patches and adding them as additional training samples to the input data. However, these techniques involve augmenting data with a large number of transformation parameters, which produces many times more additional training samples, most of which are not informative enough to be useful or even irrelevant. This approach also require additional computational resources to handle the enormous amount of additional training data.

Another common approach is to extract random patches, and use them as additional training samples to the input data. However, small patches generated from scene images are more object-centric than scene-centric and do not explicitly encode the holistic information about the entire scene, thereby increasing inter-class similarities when similar objects appear in different scene categories. This can have a negative effect on the accuracy and robustness of the classification model. The choice of an appropriate data strategy is therefore a crucial aspect in producing a reasonably accurate and robust classification model, especially with a limited number of additional training sample or when handling imbalanced datasets.

SUMMARY

Exemplary embodiments of the present disclosure are directed to methods for image classification using limited training data through holistically engineered data augmentation which generates new representations of the input data using differential geometry and preserves the holistic information contained in the image, and a convolutional neural network (CNN)-based deep fusion architecture that fuses class-specific CNN activations produced by the convolutional layers from different modalities and generates stronger and more discriminative feature maps than a traditional CNN. Embodiments of the disclosure generate a new representation of the input data, referred to hereinbelow as a geometric embedding, and use this representation together with the original data as input into a deep fusion CNN based architecture for image classification.

According to an embodiment of the disclosure, there is provided a computer-implemented method for digital image classification and localization, including receiving a digital image of a biological organism from an imaging apparatus, the digital image comprising a plurality of intensities on a 2-dimensional (2D) grid of points, generating a plurality of discriminative representations of the received digital image by extracting dominant characteristics of the image from three different viewpoints, where the plurality of discriminative representations form a 3-dimensional (3D) digital image, combining the 3D digital image with the received 2D digital image in a convolutional neural network that outputs a 3-channel feature map that localizes image abnormalities in each of the three channels and includes a detection confidence that each abnormalities is a neoplasm, providing the 3-channel feature map to a controller of a robotic surgical device where the robotic surgical device uses the 3-channel feature map to locate the neoplasm within the biological organism in a surgical procedure for treating the neoplasm.

According to a further aspect of the invention, generating a plurality of discriminative representations of the received digital image includes computing a 2-dimensional normal field $n(x,y)=(V_a \times V_b)/|V_a \times V_b|$ from the received 2D digital image, where $V_a=p(x-r,y)-p(x+r,y)$, $V_b=p(x,y-r)-p(x,y+r)$, and $p(x,y)=[x, y, I(x,y)]$ is a 3D vector field, where $I(x,y)$ is the intensity of pixel $(x,y)$ in the received 2D digital image, and generating the 3D digital image $GE(x,y)=[O_1(x,y), O_2(x,y), O_3(x,y)]$ by calculating three angular orientation fields $O_1$, $O_2$, and $O_3$ by taking an inverse tangent of a projection of the normal vector $n(x,y)$ of each pixel onto each of three principal direction vectors $\lambda_1, \lambda_2, \lambda_3$, where $O_1(x,y)=\arctan(n(x,y)\cdot \lambda_1)$, $O_2(x,y)=\arctan(n(x,y)\cdot \lambda_2)$, and $O_3(x,y)=\arctan(n(x,y)\cdot \lambda_3)$.

According to a further aspect of the invention, the convolutional neural network (CNN) includes two CNN models, one that processes data of the received 2D digital image and the other that processes data of the 3D digital image, where the CNN comprises a plurality of convolutional layers for each of the two CNNs alternating with a plurality of fusion layers that combine convolutional layer output for the 3D digital image with convolutional layer output for the received digital image, and a plurality of fully connected layers that have connections to all activations in a previous layer.

According to a further aspect of the invention, given a batch A of feature maps output from the CNN that processes the received 2D digital image, and a batch B of feature maps output from the CNN that processes the 3D digital image, combining the 3D digital image with the received digital image in a convolutional neural network comprises, for each feature map in batch B, generating a fusion map equal to the feature map in batch B plus a mean of class-specific feature maps in batch A, where class-specific maps of batch A represents features in a same class as those of a feature map in batch B.

According to a further aspect of the invention, feature maps in both batch A and batch B are sorted with respect to their classes, and features maps of batch B which belong to a same class are summed.

According to another aspect of the invention, there is provided a non-transitory program storage device readable by a computer, tangibly embodying a program of instructions executed by the computer to perform the method steps for digital image classification and localization.

DETAILED DESCRIPTION OF EXEMPLARY EMBODIMENTS

Figure 1:
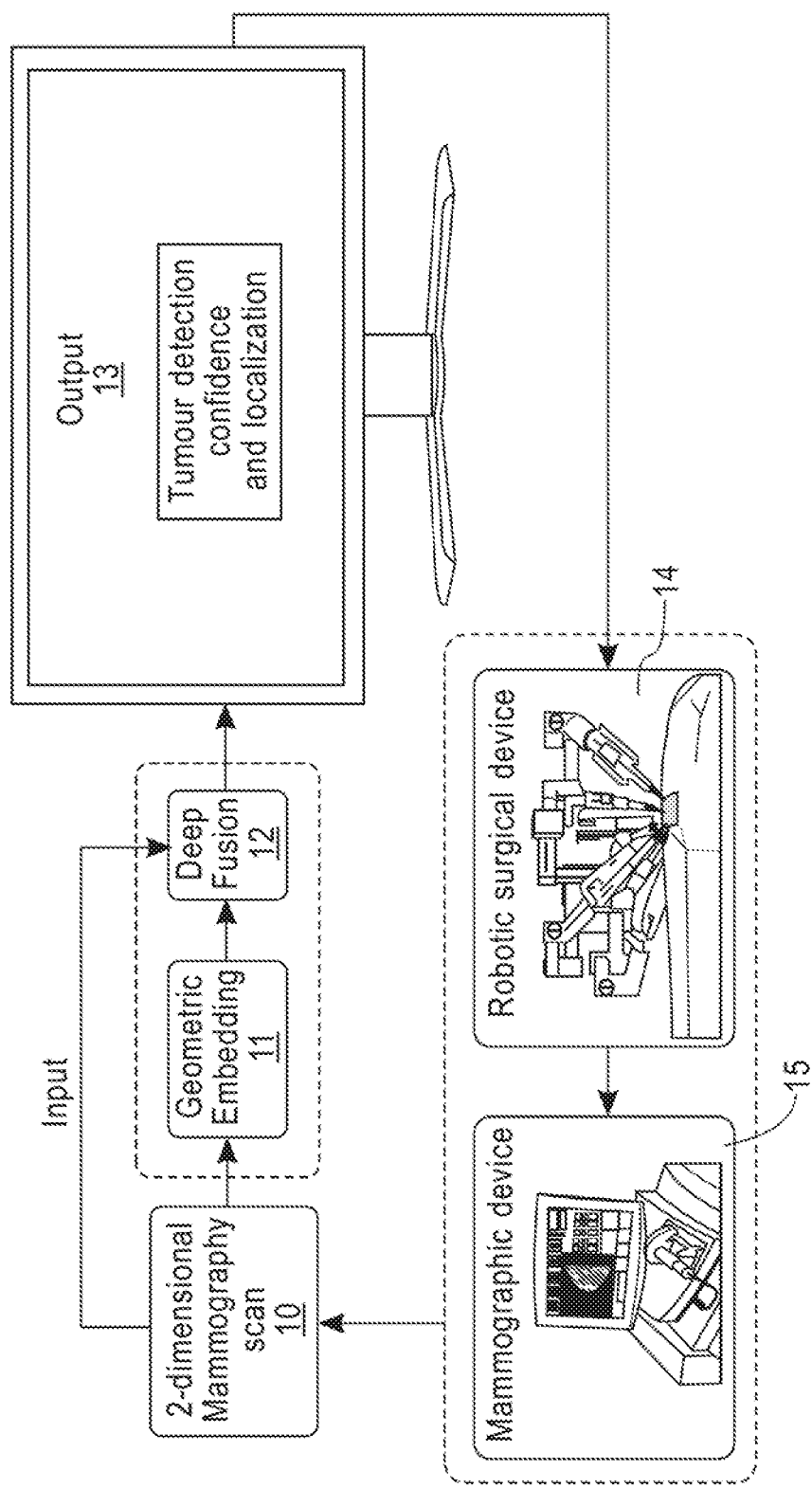
FIG. 1 is a schematic diagram of a system for classifying and localizing mammographic images, according to embodiments of the disclosure.

Exemplary embodiments of the disclosure as described herein generally provide systems and methods for image classification using limited training data. While embodiments are susceptible to various modifications and alternative forms, specific embodiments thereof are shown by way of example in the drawings and will herein be described in detail. It should be understood, however, that there is no intent to limit the disclosure to the particular forms disclosed, but on the contrary, the disclosure is to cover all modifications, equivalents, and alternatives falling within the spirit and scope of the disclosure.

As used herein, the term "image" refers to multi-dimensional data composed of discrete image elements (e.g., pixels for 2-dimensional images and voxels for 3-dimensional images). The image may be, for example, an image of a subject collected by any imaging system known to one of skill in the art. Although an image can be thought of as a function from $R^3$ to R, methods of the disclosure are not limited to such images, and can be applied to images of any dimension, e.g., a 2-dimensional picture or a 3-dimensional volume. For a 2- or 3-dimensional image, the domain of the image is typically a 2- or 3-dimensional rectangular array, wherein each pixel or voxel can be addressed with reference to a set of 2 or 3 mutually orthogonal axes. The terms "digital" and "digitized" as used herein will refer to images or volumes, as appropriate, in a digital or digitized format acquired via a digital acquisition system or via conversion from an analog image.

Exemplary embodiments of the present disclosure can provide a system and method for image classification and localization. This is achieved by a holistically engineered data transformation method, referred to hereinbelow as geometric embedding, which generates three novel representations of a one-dimensional image and shows the dominant characteristics of the input image from three different views, and a CNN-based architecture, which uses the geometric embedding of images and produces tumor identification as well as its localization within the image.

For the purposes of exposition, embodiments of the disclosure that can be used to classify and localise neoplasms such as tumor cavities in mammographic images will be described. However, this example is non-limiting, and embodiments of the disclosure can be used for other applications of image classification.

FIG. 1 is a schematic diagram of a system for classifying and localizing mammographic images, according to embodiments of the disclosure. Referring now to the figure, an initial 2-dimensional (2D) mammography scan 10 received from a mammographic device 15 is provided to a geometric embedding application 11 and a deep fusion CNN 12 according to an embodiment of the disclosure. The geometric embedding application 11 processes the 1D mammography scan 10 into geometric embedding vector, and provides it to the deep fusion CNN 12, which combines the geometric embedding vector with the 2D mammography scan 10 to output a 3-channel feature map 13 that includes the tumor detection confidence and localizes the tumor in each of the three channels. The 3-channel feature map 13 can be effectively be used within a closed control loop of a robotic surgical device 14 for the automatic removal of tumor cavities, and to control the mammographic device 15 to acquire more images 10.

Geometric Embedding:

According to embodiments of the disclosure, geometric embedding of a feature map generates three representations of an input one-dimensional image and includes three angular orientation fields computed with respect to three global viewpoints defined by the three principal directions of the data. A geometric embedding according to embodiment can show the dominant characteristics of the input image from three different viewpoints.

Figure 2:
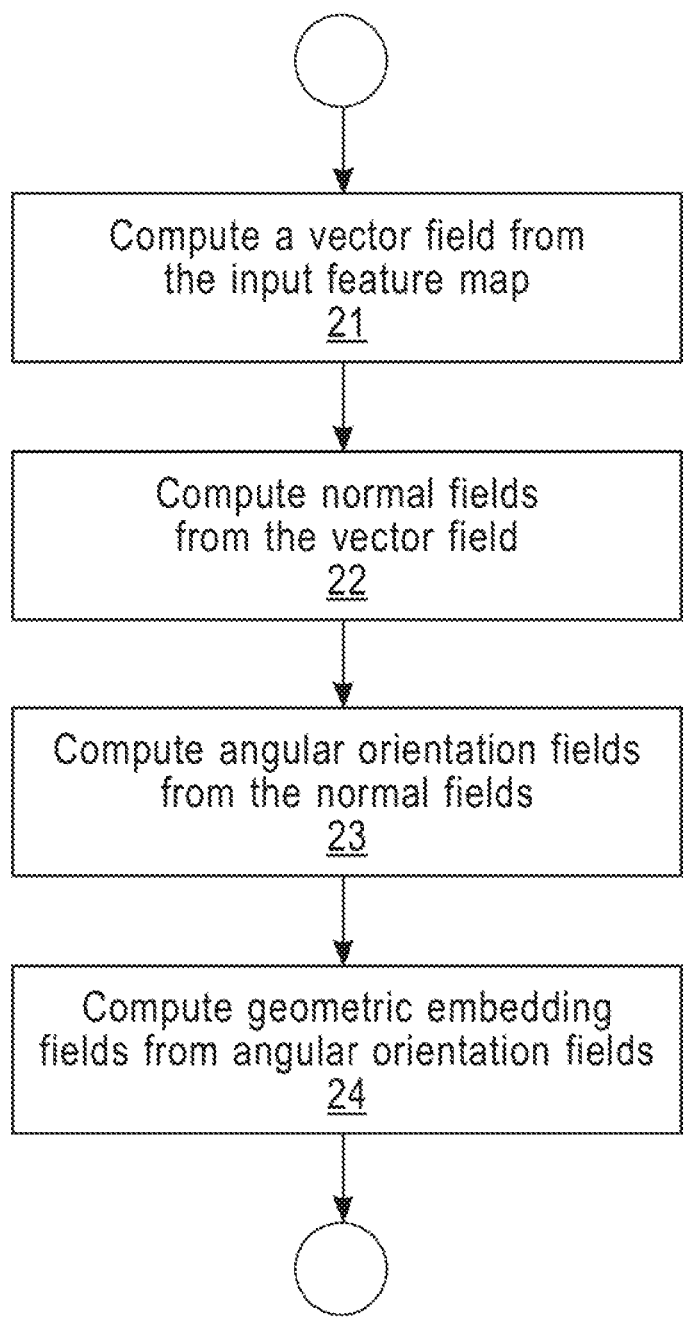
FIG. 2 is a flow chart of a geometric embedding an input one dimensional image, according to embodiments of the disclosure.

A geometric embedding according to embodiment of an input one dimensional image includes the following steps, as illustrated by the flow chart of FIG. 2. Given a 2D feature map received as input, a method according to an embodiment computes, at step 21, a vector field $p(x,y)=[x, y, I(x,y)]$ in which each 2D pixel is defined as a 3-dimensional vector given by the spatial coordinates in the image space and its intensity value $I(x,y)$. At step 22, a normal field $n(x,y)$ is computed from $$V_a = p(x-r,y) - p(x+r,y);$$

$$V_b = p(x,y-r) - p(x,y+r)$$

$$n(x,y) = (V_a \times V_b)/|V_a \times V_b|$$

using cross products between vectors defined along top and bottom, and left and right pixels for a given pixel in the vector field. The variable r is a user-defined parameter which represents the size of local neighborhood used to compute the vectors $V_a$ and $V_b$. For example, r=5 represents a local neighborhood of 5-pixels with respect to the pixel location (x,y). The normal field is used at step 23 to calculate three angular orientation field $O_1$, $O_2$, and $O_3$, by taking an inverse tangent of the projection of the normal vector of a pixel onto each of the three principal direction vectors $\lambda_1$, $\lambda_2$, $\lambda_3$:

$$O_1(x,y) = \arctan(n(x,y) \cdot \lambda_1);$$

$$O_2(x,y) = \arctan(n(x,y) \cdot \lambda_2);$$

$$O_3(x,y) = \arctan(n(x,y) \cdot \lambda_3).$$

Each $O_i$ represents a 2D feature map, where the value at a pixel location (x,y) encodes the angular orientation with respect to the normal at that location $n(r,y)$ and the ith principal moment of the image $\lambda_i$. At step 24, the angular orientation fields are stacked along the third dimension to generate a 3D feature map $GE(x,y)=[O_1(x,y), O_2(x,y), O_3(x,y)]$, referred to herein as a geometric embedding. There is one 3D image GE computed for a 2D input image. Features which qualitatively appear in different views of the geometric embedding differ from each other and thus provide complimentary information for tumor identification and localization.

A geometric embedding according to embodiments of the disclosure is a 3D vector field with dimensions w×h×3, where w is a width in pixels and h is a height in pixels, that can be visualized with a 3D vector associated to each (x,y) location in a 2D space. Another way to understand the structure of geometric embedding is to consider the example of a color RGB image, which has three channels (R, G, B) stacked together, along a third dimension, and each channel is a 2D feature map defined by its width (w), height (h), and pixel values at (x,y) locations. The structure of a geometric embedding according to embodiments of the disclosure is similar to the RGB image, where O1, O2 and O3 channels replace R, G and B channels, respectively.

CNN-Based Architecture

According to exemplary embodiments, another aspect is a CNN-based architecture for tumor identification and localization. Specifically, a CNN-based architecture includes two CNN models. One model trains on the original data and the other model trains on the geometric embedding of the original data, in which the weights of all the convolutional and fully-connected layers are initialized from Gaussian distributions.

Figure 3:
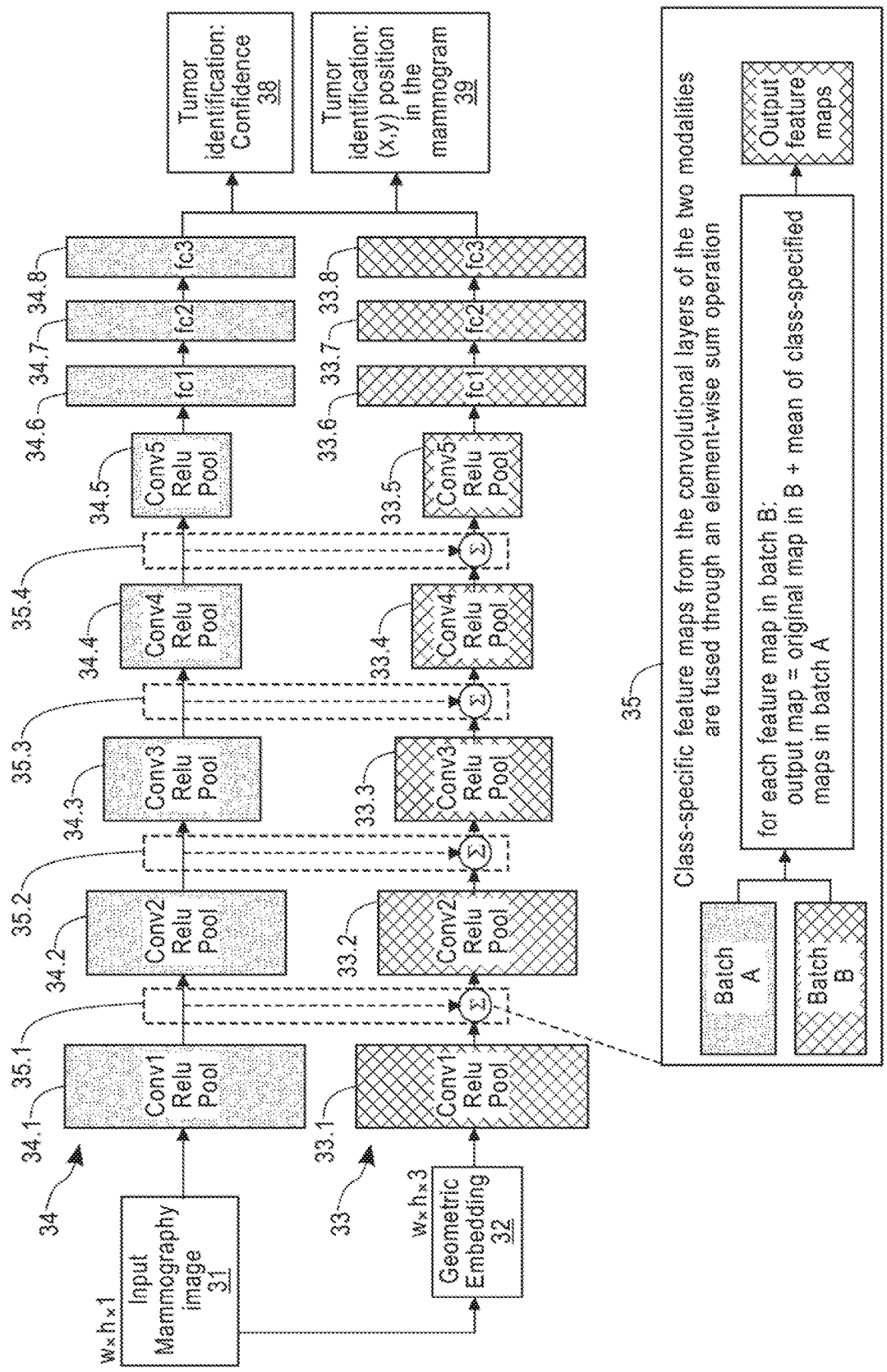
FIG. 3 illustrates a method of fusing the activations of the convolutional layers of a two CNN models, according to embodiments of the disclosure.

A fusion layer according to an embodiment combines the activations of the convolutional layers of the two CNN models and learns more stronger and discriminative features, which results in better classification and localization performance. A method of fusing the activations of the convolutional layers of the two CNN models is illustrated in FIG. 3. FIG. 3 depicts 2 CNN models 33 and 34, that include nodes 33.$i$ and 34.$i$, that alternate with fusion layers 35.$j$. According to an embodiment, i=1 to 5 and j=1 to 4, but embodiments are not limited to that number of layers. The input to the CNN model 34 is the original mammography image 31, a 2D image of size w×h×1 pixels, and the input to CNN model 33 is the geometric embedding image 32 calculated from the input mammography image 31, which is a 3D image of size w×h×3 pixels.

Each of the nodes 33.$i$ and 34.$i$ includes a convolutional layer Conv$i$, that includes a standard rectified linear unit layer Relu and a standard max pooling layer Pool. Each convolutional layer Conv$i$ includes a set of learnable filters, which have a small receptive field in the input volume. During a forward pass, each filter is convolved across the width and height of the input volume, computing the dot product between the entries of the filter and the input and producing a 2-dimensional activation map of that filter. As a result, the network learns filters that activate when it detects some specific type of feature at some spatial position in the input. The rectified linear units layers Relu applies a non-saturating activation function convolutional layer. The standard max pooling layers Pool perform non-linear downsampling using max pooling, which partitions the output of the rectified linear units layers into a set of non-overlapping rectangles and, for each such sub-region, outputs the maximum.

The fusion layers 35.$i$ fuse class-specific feature maps from the output of the nodes of the two CNN modalities 33, 34 through an element-wise sum operation. As indicated in box 35, given Batch A and Batch B respectively output from each CNN modality 33, 34, for each feature map in batch B, the output map is equal to the original map in B plus the mean of the class-specific maps in Batch A. In box 35, Batch A represents the feature maps of the original input data along the top layer of the CNN model, and Batch B represents the feature maps of a geometric embedding according to an embodiment along the bottom layer of the CNN model. Class-specific maps of Batch A represents the features which have the same class as that of a feature map in Batch B.

For the case of cancer classification, digital mammography data can be divided into two classes: a class that represents mammography scans which are negative, i.e., scans with no evidence of cancer, and typically labeled "0"; and a class that represents positive mammography scans which contain visual evidences of cancer tumors, typically labeled "1". Features refer to the output produced by an individual layer in the CNN architecture. Typically, these features are in the form of 2-dimensional maps composed of real-valued numbers in the case of convolutional layers. In the case of fully-connected layers of the CNN, these features are usually 1-dimensional row vectors containing real-valued numbers.

When feature maps from the top layer of the CNN are combined with feature maps from the bottom layer of the CNN model, the feature maps are sorted with respect to their classes, and features which belong to the same class are summed. Because input images are randomly drawn from the training data, samples (in Batch A/B) are obtained which are uneven in terms of their classes, e.g., there may be 7 samples from class A and 3 samples from class B. Therefore, it is useful to add the features with similar classes, and not in a random fashion, to ensure that irrelevant information is not mixed in the CNN model during the fusion, e.g., features of a building are not added to features of a car.

After several convolutional, standard rectified linear unit, and max pooling layers, the high-level reasoning in the neural network is completed via several fully connected layers. CNN models 33 and 34 include fully connected layers 33.6, 33.7, 33.8 and 34.6, 34.7, 34.8, respectively, that have connections to all activations in the previous layer, and have activations that are computed with a matrix multiplication followed by a bias offset. Although 3 fully connected layers in the figure, embodiments are not limited to that number of layers. The final output of the CNN models 33 and 34 is a tumor identification 38 with a % confidence, and a tumor localization 39, that provides an (x, y) position of the tumor in the mammogram.

Experimental Results

Embodiments of the disclosure were evaluated a digital mammography dataset for a special scenario where the data set is hugely imbalanced, i.e., the under-represented class is 1% of the over-represented class. The results indicate that the accuracy decreases when the data is augmented through traditional geometrical transformations such as mirror, rotation or random crop transformations, which degrades the image classification performance. On the other hand, data augmentation through the geometric embedding and a deep fusion architecture according to embodiments of the disclosure produces superior accuracy and significant reduction in the test loss compared to the baseline CNN models. The use of rotated versions and random crops of the original data caused a negative effect on the accuracy of a traditional CNN model for image classification when the available training data is limited, while methods according to embodiments yielded at least a 4% accuracy improvement over a traditional CNN and conventional data augmentation techniques for image classification.

Geometric embedding enriches the training samples with complimentary information that is more discriminative than training samples produced through affine/geometric transformations, such as in-plane rotations, translations, flipping, etc., where the image data remains unchanged. In addition, geometric embedding preserves the holistic information contained in the image. This minimizes the chances of increasing inter-class similarities compared to methods which use image patches as additional training samples. A fusion architecture according to an embodiment learns stronger and more discriminative feature maps compared to traditional CNNs, thus yielding higher accuracy. Methods and systems according to embodiments can effectively handle insufficient labelled data due to small or imbalanced data sets for training CNN models for tumor identification and localization, and can be effectively be used within a closed control loop of a robotic surgical device for the automatic removal of tumor cavities.

System Implementations

It is to be understood that embodiments of the present disclosure can be implemented in various forms of hardware, software, firmware, special purpose processes, or a combination thereof. In one embodiment, an embodiment of the present disclosure can be implemented in software as an application program tangible embodied on a computer readable program storage device. The application program can be uploaded to, and executed by, a machine comprising any suitable architecture. Furthermore, it is understood in advance that although this disclosure includes a detailed description on cloud computing, implementation of the teachings recited herein are not limited to a cloud computing environment. Rather, embodiments of the present disclosure are capable of being implemented in conjunction with any other type of computing environment now known or later developed. An automatic troubleshooting system according to an embodiment of the disclosure is also suitable for a cloud implementation.

Cloud computing is a model of service delivery for enabling convenient, on-demand network access to a shared pool of configurable computing resources (e.g. networks, network bandwidth, servers, processing, memory, storage, applications, virtual machines, and services) that can be rapidly provisioned and released with minimal management effort or interaction with a provider of the service. This cloud model may include at least five characteristics, at least three service models, and at least four deployment models.

Characteristics are as follows:

On-demand self-service: a cloud consumer can unilaterally provision computing capabilities, such as server time and network storage, as needed automatically without requiring human interaction with the service's provider.

Broad network access: capabilities are available over a network and accessed through standard mechanisms that promote use by heterogeneous thin or thick client platforms (e.g., mobile phones, laptops, and PDAs).

Resource pooling: the provider's computing resources are pooled to serve multiple consumers using a multi-tenant model, with different physical and virtual resources dynamically assigned and reassigned according to demand. There is a sense of location independence in that the consumer generally has no control or knowledge over the exact location of the provided resources but may be able to specify location at a higher level of abstraction (e.g., country, state, or datacenter).

Rapid elasticity: capabilities can be rapidly and elastically provisioned, in some cases automatically, to quickly scale out and rapidly released to quickly scale in. To the consumer, the capabilities available for provisioning often appear to be unlimited and can be purchased in any quantity at any time.

Measured service: cloud systems automatically control and optimize resource use by leveraging a metering capability at some level of abstraction appropriate to the type of service (e.g., storage, processing, bandwidth, and active user accounts). Resource usage can be monitored, controlled, and reported providing transparency for both the provider and consumer of the utilized service.

Service Models are as follows:

Software as a Service (SaaS): the capability provided to the consumer is to use the provider's applications running on a cloud infrastructure. The applications are accessible from various client devices through a thin client interface such as a web browser (e.g., web-based email). The consumer does not manage or control the underlying cloud infrastructure including network, servers, operating systems, storage, or even individual application capabilities, with the possible exception of limited user-specific application configuration settings.

Platform as a Service (PaaS): the capability provided to the consumer is to deploy onto the cloud infrastructure consumer-created or acquired applications created using programming languages and tools supported by the provider. The consumer does not manage or control the underlying cloud infrastructure including networks, servers, operating systems, or storage, but has control over the deployed applications and possibly application hosting environment configurations.

Infrastructure as a Service (IaaS): the capability provided to the consumer is to provision processing, storage, networks, and other fundamental computing resources where the consumer is able to deploy and run arbitrary software, which can include operating systems and applications. The consumer does not manage or control the underlying cloud infrastructure but has control over operating systems, storage, deployed applications, and possibly limited control of select networking components (e.g., host firewalls).

Deployment Models are as follows:

Private cloud: the cloud infrastructure is operated solely for an organization. It may be managed by the organization or a third party and may exist on-premises or off-premises.

Community cloud: the cloud infrastructure is shared by several organizations and supports a specific community that has shared concerns (e.g., mission, security requirements, policy, and compliance considerations). It may be managed by the organizations or a third party and may exist on-premises or off-premises.

Public cloud: the cloud infrastructure is made available to the general public or a large industry group and is owned by an organization selling cloud services.

Hybrid cloud: the cloud infrastructure is a composition of two or more clouds (private, community, or public) that remain unique entities but are bound together by standardized or proprietary technology that enables data and application portability (e.g., cloud bursting for load balancing between clouds).

A cloud computing environment is service oriented with a focus on statelessness, low coupling, modularity, and semantic interoperability. At the heart of cloud computing is an infrastructure comprising a network of interconnected nodes.

Figure 4:
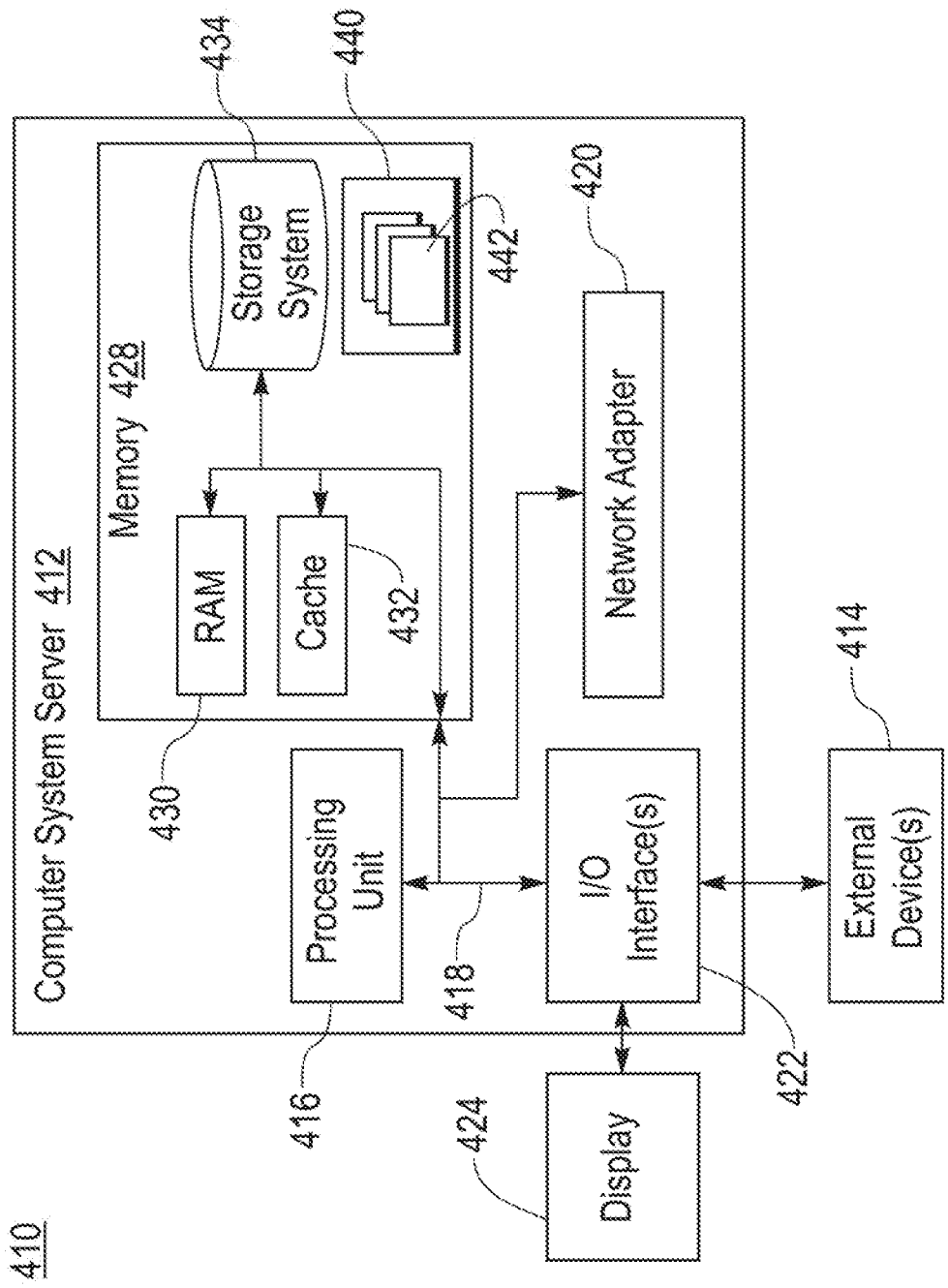
FIG. 4 is a schematic of an exemplary cloud computing node that implements an embodiment of the disclosure.

Referring now to FIG. 4, a schematic of an example of a cloud computing node is shown. Cloud computing node 410 is only one example of a suitable cloud computing node and is not intended to suggest any limitation as to the scope of use or functionality of embodiments of the disclosure described herein. Regardless, cloud computing node 410 is capable of being implemented and/or performing any of the functionality set forth herein above.

In cloud computing node 410 there is a computer system/server 412, which is operational with numerous other general purpose or special purpose computing system environments or configurations. Examples of well-known computing systems, environments, and/or configurations that may be suitable for use with computer system/server 412 include, but are not limited to, personal computer systems, server computer systems, thin clients, thick clients, handheld or laptop devices, multiprocessor systems, microprocessor-based systems, set top boxes, programmable consumer electronics, network PCs, minicomputer systems, mainframe computer systems, and distributed cloud computing environments that include any of the above systems or devices, and the like.

Computer system/server 412 may be described in the general context of computer system executable instructions, such as program modules, being executed by a computer system. Generally, program modules may include routines, programs, objects, components, logic, data structures, and so on that perform particular tasks or implement particular abstract data types. Computer system/server 412 may be practiced in distributed cloud computing environments where tasks are performed by remote processing devices that are linked through a communications network. In a distributed cloud computing environment, program modules may be located in both local and remote computer system storage media including memory storage devices.

As shown in FIG. 4, computer system/server 412 in cloud computing node 410 is shown in the form of a general-purpose computing device. The components of computer system/server 412 may include, but are not limited to, one or more processors or processing units 416, a system memory 428, and a bus 418 that couples various system components including system memory 428 to processor 416.

Bus 418 represents one or more of any of several types of bus structures, including a memory bus or memory controller, a peripheral bus, an accelerated graphics port, and a processor or local bus using any of a variety of bus architectures. By way of example, and not limitation, such architectures include Industry Standard Architecture (ISA) bus, Micro Channel Architecture (MCA) bus, Enhanced ISA (EISA) bus, Video Electronics Standards Association (VESA) local bus, and Peripheral Component Interconnect (PCI) bus.

Computer system/server 412 typically includes a variety of computer system readable media. Such media may be any available media that is accessible by computer system/server 412, and it includes both volatile and non-volatile media, removable and non-removable media.

System memory 428 can include computer system readable media in the form of volatile memory, such as random access memory (RAM) 430 and/or cache memory 432. Computer system/server 412 may further include other removable/non-removable, volatile/non-volatile computer system storage media. By way of example only, storage system 434 can be provided for reading from and writing to a non-removable, non-volatile magnetic media (not shown and typically called a "hard drive"). Although not shown, a magnetic disk drive for reading from and writing to a removable, non-volatile magnetic disk (e.g., a "floppy disk"), and an optical disk drive for reading from or writing to a removable, non-volatile optical disk such as a CD-ROM, DVD-ROM or other optical media can be provided. In such instances, each can be connected to bus 418 by one or more data media interfaces. As will be further depicted and described below, memory 428 may include at least one program product having a set (e.g., at least one) of program modules that are configured to carry out the functions of embodiments of the disclosure.

Program/utility 440, having a set (at least one) of program modules 442, may be stored in memory 428 by way of example, and not limitation, as well as an operating system, one or more application programs, other program modules, and program data. Each of the operating system, one or more application programs, other program modules, and program data or some combination thereof, may include an implementation of a networking environment. Program modules 442 generally carry out the functions and/or methodologies of embodiments of the disclosure as described herein.

Computer system/server 412 may also communicate with one or more external devices 414 such as a keyboard, a pointing device, a display 424, etc.; one or more devices that enable a user to interact with computer system/server 412; and/or any devices (e.g., network card, modem, etc.) that enable computer system/server 412 to communicate with one or more other computing devices. Such communication can occur via Input/Output (I/O) interfaces 422. Still yet, computer system/server 412 can communicate with one or more networks such as a local area network (LAN), a general wide area network (WAN), and/or a public network (e.g., the Internet) via network adapter 420. As depicted, network adapter 420 communicates with the other components of computer system/server 412 via bus 418. It should be understood that although not shown, other hardware and/or software components could be used in conjunction with computer system/server 412. Examples, include, but are not limited to: microcode, device drivers, redundant processing units, external disk drive arrays, RAID systems, tape drives, and data archival storage systems, etc.

Figure 5:
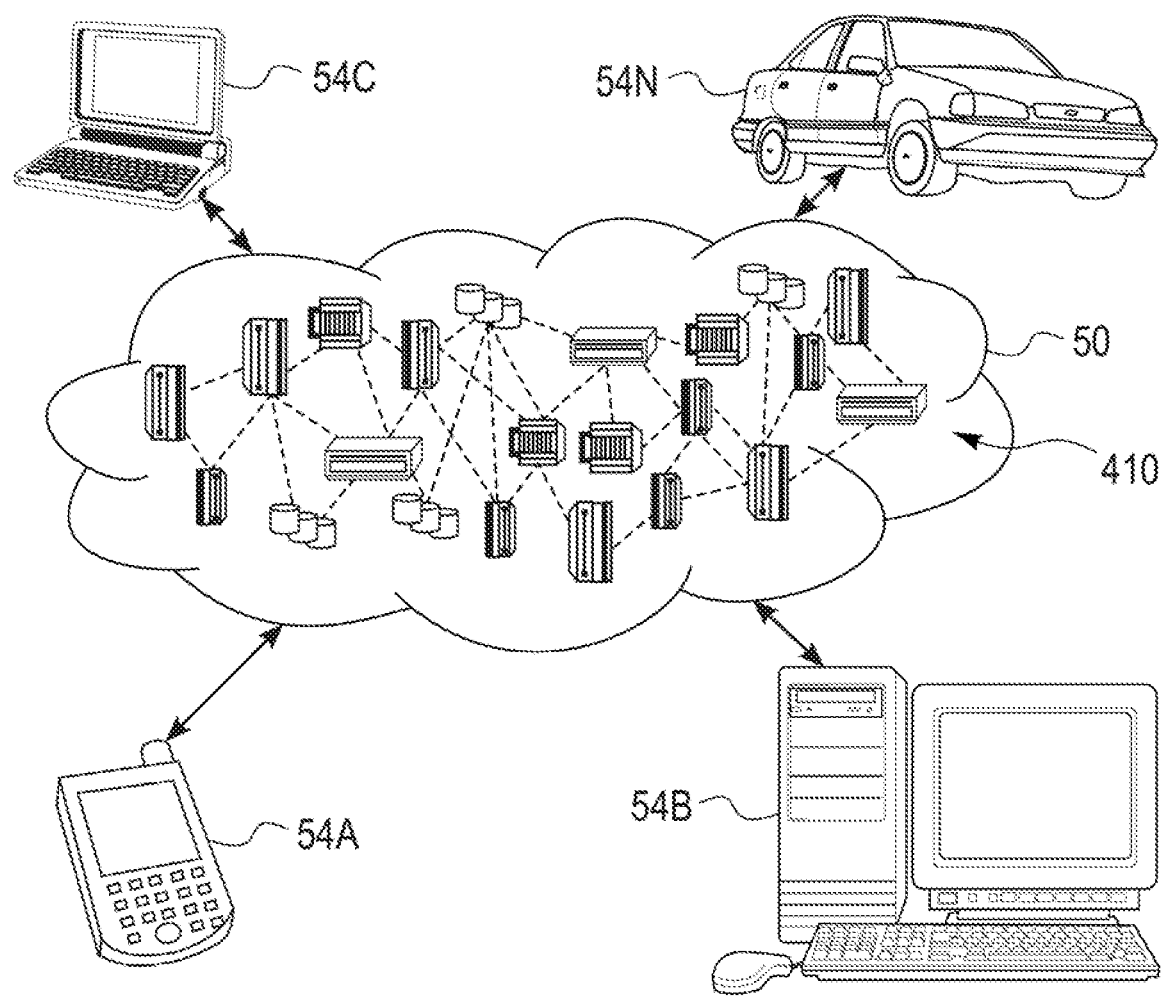
FIG. 5 shows an exemplary cloud computing environment according to embodiments of the disclosure.

Referring now to FIG. 5, illustrative cloud computing environment 50 is depicted. As shown, cloud computing environment 50 comprises one or more cloud computing nodes 400 with which local computing devices used by cloud consumers, such as, for example, personal digital assistant (PDA) or cellular telephone 54A, desktop computer 54B, laptop computer 54C, and/or automobile computer system 54N may communicate. Nodes 400 may communicate with one another. They may be grouped (not shown) physically or virtually, in one or more networks, such as Private, Community, Public, or Hybrid clouds as described hereinabove, or a combination thereof. This allows cloud computing environment 50 to offer infrastructure, platforms and/or software as services for which a cloud consumer does not need to maintain resources on a local computing device. It is understood that the types of computing devices 54A-N shown in FIG. 5 are intended to be illustrative only and that computing nodes 900 and cloud computing environment 50 can communicate with any type of computerized device over any type of network and/or network addressable connection (e.g., using a web browser).

While embodiments of the present disclosure has been described in detail with reference to exemplary embodiments, those skilled in the art will appreciate that various modifications and substitutions can be made thereto without departing from the spirit and scope of the disclosure as set forth in the appended claims.

What is claimed is:

1. A computer-implemented method for digital image classification and localization, comprising the steps of:
receiving a digital image of a biological organism from an imaging apparatus, said digital image comprising a plurality of intensities on a 2-dimensional (2D) grid of points;
generating a plurality of discriminative representations of the received digital image by extracting dominant characteristics of the image from three different viewpoints, wherein the plurality of discriminative representations form a 3-dimensional (3D) digital image;
combining the 3D digital image with the received 2D digital image in a convolutional neural network that outputs a 3-channel feature map that localizes image abnormalities in each of the three channels and includes a detection confidence that each abnormalities is a neoplasm;

providing the 3-channel feature map to a controller of a robotic surgical device wherein the robotic surgical device uses the 3-channel feature map to locate the neoplasm within the biological organism in a surgical procedure for treating the neoplasm.

2. The method of claim 1, wherein generating a plurality of discriminative representations of the received digital image comprises:

computing a 2-dimensional normal field $n(x,y)=(V_a \times V_b)/|V_a \times V_b|$ from the received 2D digital image, wherein $V_a=p(x-r,y)-p(x+r,y)$, $V_b=p(x,y-r)-p(x,y+r)$, and $p(x,y)=[x, y, I(x,y)]$ is a 3D vector field, wherein $I(x,y)$ is the intensity of pixel (x,y) in the received 2D digital image; and generating the 3D digital image $GE(x,y)=[O_1(x,y), O_2(x,y), O_3(x,y)]$ by calculating three angular orientation fields $O_1$, $O_2$, and $O_3$ by taking an inverse tangent of a projection of the normal vector $n(x,y)$ of each pixel onto each of three principal direction vectors $\lambda_1, \lambda_2, \lambda_3$, wherein $O_1(x,y)=\arctan(n(x,y) \cdot \lambda_1);$ $O_2(x,y)=\arctan(n(x,y) \cdot \lambda_2);$ and $O_3(x,y)=\arctan(n(x,y) \cdot \lambda_3).$ 3. The method of claim 1, wherein the convolutional neural network (CNN) includes two CNN models, one that processes data of the received 2D digital image and the other that processes data of the 3D digital image, wherein the CNN comprises a plurality of convolutional layers for each of the two CNN's alternating with a plurality of fusion layers that combine convolutional layer output for the 3D digital image with convolutional layer output for the received digital image, and a plurality of fully connected layers that have connections to all activations in a previous layer.

4. The method of claim 3, wherein, given a batch A of feature maps output from the CNN that processes the received 2D digital image, and a batch B of feature maps output from the CNN that processes the 3D digital image, combining the 3D digital image with the received digital image in a convolutional neural network comprises, for each feature map in batch B, generating a fusion map equal to the feature map in batch B plus a mean of class-specific feature maps in batch A, wherein class-specific maps of batch A represents features in a same class as those of a feature map in batch B.

5. The method of claim 4, wherein feature maps in both batch A and batch B are sorted with respect to their classes, and features maps of batch B which belong to a same class are summed.

6. A non-transitory program storage device readable by a computer, tangibly embodying a program of instructions executed by the computer to perform the method steps for digital image classification and localization, the method comprising the steps of:

receiving a digital image of a biological organism from an imaging apparatus, said digital image comprising a plurality of intensities on a 2-dimensional (2D) grid of points;

generating a plurality of discriminative representations of the received digital image by extracting dominant characteristics of the image from three different viewpoints, wherein the plurality of discriminative representations form a 3-dimensional (3D) digital image;

combining the 3D digital image with the received 2D digital image in a convolutional neural network that outputs a 3-channel feature map that localizes image abnormalities in each of the three channels and includes a detection confidence that each abnormalities is a neoplasm;

providing the 3-channel feature map to a controller of a robotic surgical device wherein the robotic surgical device uses the 3-channel feature map to locate the neoplasm within the biological organism in a surgical procedure for treating the neoplasm.

7. The computer readable program storage device of claim 6, wherein generating a plurality of discriminative representations of the received digital image comprises:

computing a 2-dimensional normal field $n(x,y)=(V_a \times V_b)/|V_a \times V_b|$ from the received 2D digital image, wherein $V_a=p(x-r,y)-p(x+r,y)$, $V_b=p(x,y-r)-p(x,y+r)$, and $p(x,y)=[x, y, I(x,y)]$ is a 3D vector field, wherein $I(x,y)$ is the intensity of pixel (x,y) in the received 2D digital image; and generating the 3D digital image $GE(x,y)=[O_1(x,y), O_2(x,y), O_3(x,y)]$ by calculating three angular orientation fields $O_1$, $O_2$, and $O_3$ by taking an inverse tangent of a projection of the normal vector $n(x,y)$ of each pixel onto each of three principal direction vectors $\lambda_1, \lambda_2, \lambda_3$, wherein $O_1(x,y)=\arctan(n(x,y)X) \cdot \lambda_1);$ $O_2(x,y)=\arctan(n(x,y) \cdot \lambda_2);$ and $O_3(x,y)=\arctan(n(x,y) \cdot \lambda_3).$ 8. The computer readable program storage device of claim 6, wherein the convolutional neural network (CNN) includes two CNN models, one that processes data of the received 2D digital image and the other that processes data of the 3D digital image, wherein the CNN comprises a plurality of convolutional layers for each of the two CNNs alternating with a plurality of fusion layers that combine convolutional layer output for the 3D digital image with convolutional layer output for the received digital image, and a plurality of fully connected layers that have connections to all activations in a previous layer.

9. The computer readable program storage device of claim 8, wherein, given a batch A of feature maps output from the CNN that processes the received 2D digital image, and a batch B of feature maps output from the CNN that processes the 3D digital image, combining the 3D digital image with the received digital image in a convolutional neural network comprises, for each feature map in batch B, generating a fusion map equal to the feature map in batch B plus a mean of class-specific feature maps in batch A, wherein class-specific maps of batch A represents features in a same class as those of a feature map in batch B.

10. The computer readable program storage device of claim 9, wherein feature maps in both batch A and batch B are sorted with respect to their classes, and features maps of batch B which belong to a same class are summed.

* * * * *